United States Patent
Aoki et al.

(10) Patent No.: US 7,087,764 B2
(45) Date of Patent: Aug. 8, 2006

(54) PROCESS FOR PRODUCING ARYLSULFENYL HALIDE

(75) Inventors: Tsutomu Aoki, Sennan (JP); Toshiro Konoike, Amagasaki (JP)

(73) Assignee: Shionogi & Co., Ltd., Osaka (JP)

( * ) Notice: Subject to any disclaimer, the term of this patent is extended or adjusted under 35 U.S.C. 154(b) by 237 days.

(21) Appl. No.: 10/366,356

(22) Filed: Feb. 14, 2003

(65) Prior Publication Data

US 2003/0195363 A1 Oct. 16, 2003

Related U.S. Application Data

(62) Division of application No. 09/646,272, filed as application No. PCT/JP99/02007 on Apr. 15, 1999, now abandoned.

(30) Foreign Application Priority Data

Apr. 16, 1998 (JP) ................. 10-106119

(51) Int. Cl.
*C07D 233/54* (2006.01)
(52) U.S. Cl. ............... 548/325.1; 568/18; 568/38; 568/56; 568/74
(58) Field of Classification Search ........... 568/18, 568/38, 56, 74; 548/325.1
See application file for complete search history.

(56) References Cited

U.S. PATENT DOCUMENTS

| | | | |
|---|---|---|---|
| 3,084,196 A | | 4/1963 | Laufer |
| 4,304,735 A | * | 12/1981 | Durden, Jr. ............... 560/312 |
| 5,169,961 A | * | 12/1992 | Dickman et al. ........... 549/57 |

FOREIGN PATENT DOCUMENTS

| | | |
|---|---|---|
| EP | 094821 | 11/1983 |
| EP | 0 741 129 | * 11/1996 |
| JP | 47-21983 | 6/1972 |
| JP | 6-56760 | 3/1994 |
| WO | 96/10019 | 4/1996 |
| WO | 98/29395 | 7/1998 |

OTHER PUBLICATIONS

Dirk et al, J. Org. Chem., vol. 50, 2395-2397, 1985.*
Biehl et al, J. Org. Chem., vol. 51, 5157-5160, 1986.*
Bochis et al, J. med. Chem., vol. 24, 1483-1487, 1981.*
Bochis et al, J. Med. Chem., 1981, 24, 1483-1487.*
Tokitoh et al., Tetrahedron Letters, 33(39), pp. 5819-5822 (1992).
Chem. Abstr., 59, Abstract No. 9897a (1963).
Dandin et al., Chem. Abstr., 52, Abstract No. 8071a (1956).
Crowell et al., Journal of Fluorine Chemistry, 21(4), pp. 469-477 (1982).

* cited by examiner

*Primary Examiner*—Shailendra Kumar
(74) *Attorney, Agent, or Firm*—Wenderoth, Lind & Ponack, L.L.P.

(57) ABSTRACT

A process for producing a compound of the formula (II):

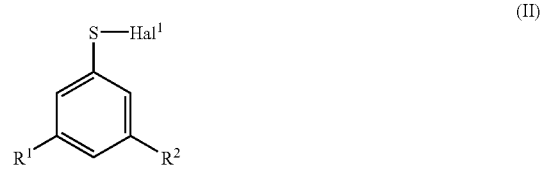

(II)

wherein $Hal^1$ represents halogen and $R^1$ and $R^2$ each independently represents halogen, alkyl, alkoxy, nitro or cyano, which comprises allowing a halogenating agent to react with a compound of the formula (I):

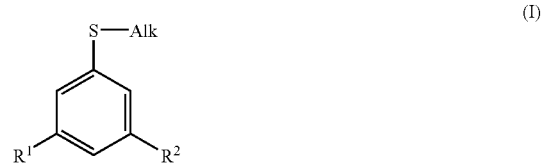

(I)

wherein Alk represents branched alkyl and $R^1$ and $R^2$ are as defined above.

4 Claims, No Drawings

PROCESS FOR PRODUCING ARYLSULFENYL HALIDE

This is a divisional of Ser. No. 09/646,272, filed Sep. 15, 2000, now abandoned which is a 371 of PCT/JP99/02007, filed Apr. 15, 1999.

TECHNICAL FIELD

This invention relates to a process for producing arylsulfenyl halide and a precursor thereof, alkyl aryl sulfide, which are useful as starting materials of a medicament, especially, an antiviral agent or an agent for treatment of AIDS.

BACKGROUND ART

A compound of the formula (IV):

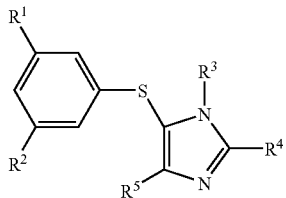

(IV)

wherein $R^1$ and $R^2$ each independently represents halogen, alkyl, alkoxy, nitro or cyano, $R^3$ represents hydrogen or an organic residue, $R^4$ represents an organic residue and $R^5$ represents hydrogen or an organic residue, is known to be pharmacologically active, useful as an antiviral agent or an agent for treatment of AIDS (WO 96/10019).

WO 96/10019 has disclosed the compound of the formula (IV) prepared through the condensation of thiophenol or disulfide and 4-halogenoimidazole derivatives. However, this reaction requires the use of a strong base such as lithium hydride, sodium hydride or potassium hydride. Moreover, the reaction must be carried out under heating because it does not proceed at room temperature. This reaction is, therefore, inappropriate for industrial process. We have already filed an application concerning the new synthetic route for stable supply of the compound of the formula (IV) (PCT/JP97/04708). It is necessary to establish a process for producing a compound of the formula (II):

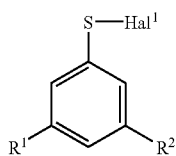

(II)

wherein $Hal^1$ represents halogen and $R^1$ and $R^2$ are as defined above, one of the starting materials used in the new synthetic route, which is applicable to a convenient, economical and large-scale production.

On the other hand, some processes for producing a similar compound to that of the formula (II) of the present invention have been known. Usually used process for producing arylsulfenyl halide is a process which comprises allowing a halogenating agent to react with a disulfide derivative prepared by the oxidization of an aromatic thiol derivative. The process for preparing the disulfide derivative from the aromatic thiol derivative has been described in, for example, Chem. Ind., 501 (1964), Synthesis-stuttgart, (5), 378–380 (1989), J. Organomet. Chem., 368 (3), 295–302 (1989) and Tetrahedron Letter, 31 (35), 5007–5010 (1990). The process which comprises allowing the halogenating agent to react with the disulfide derivative has been described in, for example, Org. Synth., II, 455, (1943).

Another known method is the process which comprises allowing the halogenating agent to react with the sulfide derivative substituted with benzyl or the like which is prepared from the aromatic thiol derivative. The process for preparing the sulfide derivatives substituted with benzyl or the like from the aromatic thiol derivatives has been described in, for example J. Org. Chem., 42 (26), 4275 (1977), Tetrahedron Letter, 635, (1969) and Chem. Pharm. Bull., 40 (8), 1986–1989 (1992). The process which comprises allowing the halogenating agent to react with the sulfide derivatives substituted with benzyl or the like has been described in, for example J. Org. Chem., 28, 1903 (1963). These conventional methods, however, require many steps for preparing the starting materials, disulfide derivatives and sulfide derivatives. The residues such as benzyl and the like are generally expensive and inappropriate for the industrial process.

Some processes for producing the aromatic thiol derivatives which are starting materials of the above-mentioned disulfide derivatives and sulfide derivatives have been known. Examples of the processes include the method which comprises allowing sulfur to react with the Grignard reagent prepared from the commercially available corresponding halide (Chem. Ber., 72, 594 (1939)), the method which comprises preparing xantate from the diazo intermediates prepared from the commercially available corresponding aniline derivatives and hydrolyzing at the next step (Org. Synth. Coll., Vol. 3, 809 (1955)), the method of the thermal rearrangement of thiourethane prepared by the acylation of easily available phenol derivatives and further hydrolysis (J. Org. Chem., Vol. 31, 3980 (1966)), and the chlorination of the methylthio derivatives prepared by the substitution reaction of the methylmercaptan with the corresponding halide and further hydrolysis (JP-A 9-40636).

These methods are, however, inappropriate for the industrial process because they not only require many steps but also proceed via unstable intermediates such as the Grignard reagents and the diazo derivatives. Indeed, these methods are difficult to apply to the industrial process because the obtained arylsulfenyl halide is expensive.

Examples of the other synthetic methods concerning arylsulfenyl halide include the process for producing arylsulfenyl halide which comprises allowing the halogenating agent to react with the alkyl aryl sulfide derivatives prepared from the halogenated benzene derivatives.

As the process for producing alkylarylsulfide, the process for producing 2,5-dichlorophenylalkylsulfide from 1,2,4-trichlorobenzene is disclosed in JP-A 9-56760. In Tetrahedron Letters, 1982, 23, 4629, the process for producing 4-chlorophenylalkylsulfide from 1,4-dichlorobenzene is disclosed.

As the process for producing arylsulfenyl halide from alkylarylsulfide, the process for producing 4-isopropoxyphenylsulfenylhalide from 4-isopropoxyphenyl isopropyl sulfide is disclosed (Synthesis, 1976, 451).

These literatures and the like do not disclose the above-described process using 3,5-dihalogenated benzene derivatives as a starting material.

In J. Org. Chem., 1980, 45, 3880–3884, 3,5-dichlorophenylsulfenylchloride is disclosed, but a process thereof is not mentioned at all.

DISCLOSURE OF INVENTION

The present inventors have studied intensively the process for producing arylsulfenyl halide, which is applicable to a convenient, economical and large-scale production and have found out the process for efficiently producing the compound of the formula (II) with a few steps under mild condition, which comprises reacting the compound of the formula (V) with the compound of the formula (VI) in the presence of a base, followed by reaction with a halogenating agent, to accomplish the present invention. Moreover, the compound of the formula (IV) have been prepared through the reaction of the compound of the formula (II) obtained above with the compound of the formula (III);

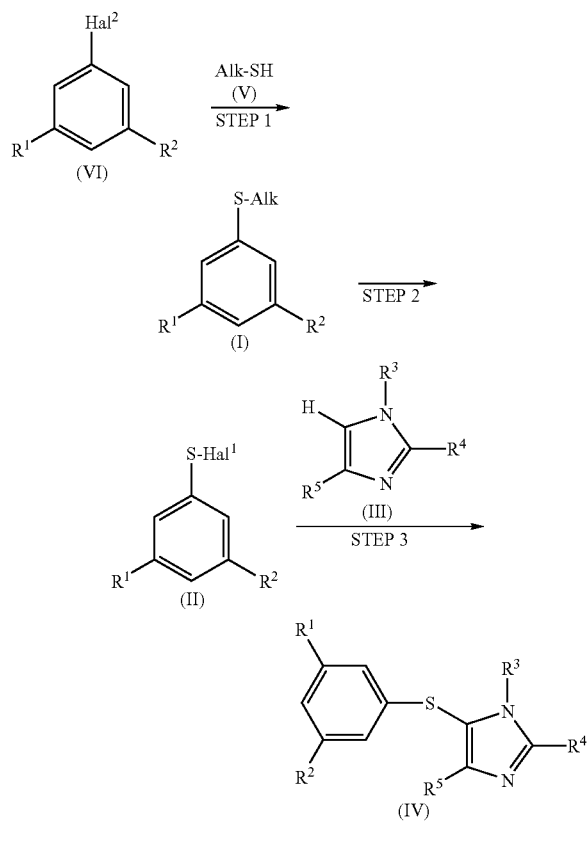

wherein Alk represents branched alkyl, $Hal^1$ and $Hal^2$ each independently represents halogen, $R^1$ and $R^2$ each independently represents halogen, alkyl, alkoxy, nitro or cyano, $R^3$ and $R^5$ each independently represents hydrogen or an organic residue and $R^4$ represents an organic residue.

BEST MODE FOR CARRYING OUT THE INVENTION

The preferable embodiments are shown below.
The present invention provides;
(1) a process for producing a compound of the formula (II):

wherein $Hal^1$ represents halogen and $R^1$ and $R^2$ each independently represents halogen, alkyl, alkoxy, nitro or cyano, which comprises allowing a halogenating agent to react with a compound of the formula (I):

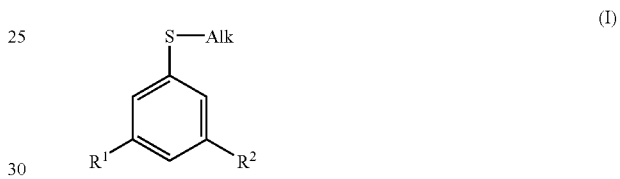

wherein Alk represents branched alkyl and $R^1$ and $R^2$ are as defined above.

Moreover, the present invention provides;
(2) a process for producing a compound of the formula (IV):

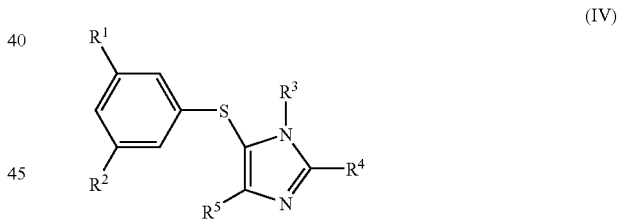

wherein $R^1$ and $R^2$ are as defined above, $R^3$ represents hydrogen or an organic residue, $R^4$ represents an organic residue and $R^5$ represents hydrogen or an organic residue, which comprises preparing a compound of the formula (II):

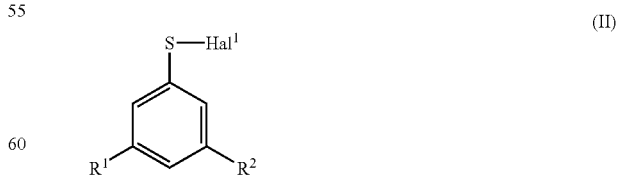

wherein $Hal^1$ represents halogen and $R^1$ and $R^2$ are as defined above, by the above-mentioned process, then reacting the compound of the formula (II) with a compound of the formula (III):

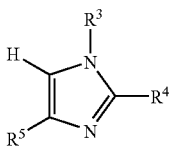

wherein $R^3$, $R^4$ and $R^5$ are as defined above.

Additionally, the present invention provides;

(3) a process for producing a compound of the formula (I):

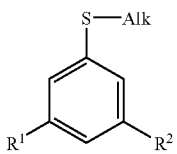

(I)

wherein Alk, $R^1$ and $R^2$ are as defined above, which comprises reacting a compound of the formula (V):

Alk-SH        (V)

wherein Alk presents as defined above, with a compound of the formula (VI):

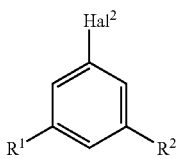

(VI)

wherein $Hal^2$ represents halogen and $R^1$ and $R^2$ are as defined above, in the presence of a base.

Moreover, the present invention provides;

(4) a process for producing a compound of the formula (II):

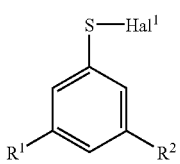

(II)

wherein $Hal^1$, $R^1$ and $R^2$ are as defined above, which comprises preparing a compound of the formula (I):

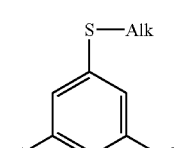

(I)

wherein Alk, $R^1$ and $R^2$ are as defined above, by the above-mentioned process, then allowing a halogenating agent to react with the compound of the formula (I).

Moreover, the present invention provides;

(5) a process for producing a compound of the formula (IV):

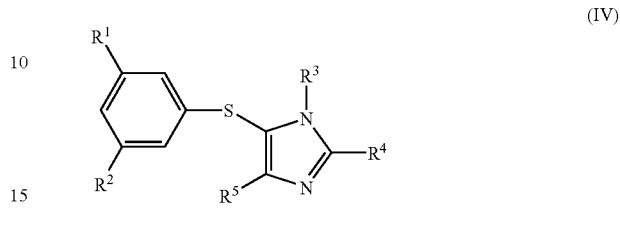

(IV)

wherein $R^1$, $R^2$, $R^3$, $R^4$ and $R^5$ are as defined above, which comprises preparing a compound of the formula (II):

(II)

wherein $Hal^1$ represents halogen and $R^1$ and $R^2$ are as defined above, by the above-mentioned process, then reacting the compound of the formula (II) with a compound of the formula (III):

(III)

wherein $R^3$, $R^4$ and $R^5$ are as defined above.

In the above-mentioned process (1) or (4), chlorine is preferred as the halogenating agent.

In the above-mentioned (3), preferred is reacting in the presence of a phase transfer catalyst. Additionally, quaternary ammonium salt or quaternary phosphonium salt is preferred as a phase transfer catalyst.

In the above-mentioned process (1) or (3), isopropyl or tert-butyl is preferred as Alk.

In any one of the above-mentioned processes (1)–(5), preferred is the process wherein $R^1$ and $R^2$ each independently represents halogen.

In the above-mentioned (2) or (5), preferred is the process wherein $R^3$ represents hydrogen or optionally substituted heteroarylalkyl, $R^4$ represents -A-X wherein A represents —$CH_2OCH_2$— or —$CH_2O$—, X represents optionally substituted aryl or —COB wherein B represents optionally substituted alkyl, optionally substituted alkoxy, optionally substituted aryl or optionally substituted amino and $R^5$ represents optionally substituted alkyl. Especially, the process wherein $R^3$ represents optionally substituted pyridylmethyl is preferred.

Further, the present invention provides the intermediate of the formula (Ia):

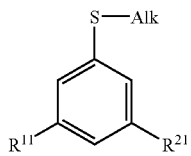

wherein $R^{11}$ and $R^{21}$ each independently represents halogen, alkyl, nitro or cyano and Alk is as defined above. Especially, the compound wherein $R^{11}$ and $R^{12}$ each independently represents halogen is preferred.

The term "an organic residue" in the present specification includes optionally substituted alkyl, optionally substituted alkenyl, optionally substituted aryl, optionally substituted arylthio, optionally substituted heteroaryl, optionally substituted heteroarylalkyl, optionally substituted aralkyl, optionally substituted acyl, optionally substituted carbamoyl, optionally substituted alkoxy, optionally substituted alkoxycarbonyl, halogen, —CH=NOH, —CH=NNH$_2$, optionally substituted aralkyloxyalkyl, optionally substituted aryloxyalkyl, optionally substituted acylalkyloxyalkyl, optionally substituted acyloxyalkyl, optionally substituted alkoxycarbonylalkyloxyalkyl, optionally substituted alkoxycarbonyloxyalkyl, optionally substituted carbamoylalkyloxyalkyl, optionally substituted carbamoyloxyalkyl and the like.

The term "alkyl" by itself or as part of (an)other substituent(s) means $C_1$–$C_{20}$ straight or branched alkyl, which includes methyl, ethyl, n-propyl, isopropyl, n-butyl, isobutyl, tert-butyl, n-pentyl, isopentyl, n-hexyl, n-heptyl, n-octyl, n-nonyl, n-decyl and the like. Especially, $C_1$–$C_6$ lower alkyl is preferred.

The term "branched alkyl" includes $C_3$–$C_8$ branched alkyl, such as isopropyl, isobutyl, tert-butyl, isopentyl and the like. Especially, isopropyl or tert-butyl is preferred.

The term "alkoxy" by itself or as a part of (an)other substituent(s) means alkyloxy, which includes methoxy, ethoxy, propoxy or tert-butoxy.

The term "alkenyl" includes $C_2$–$C_{20}$ straight or branched alkenyl, such as vinyl, allyl, propenyl, butenyl, pentenyl, hexenyl, heptenyl and the like. Especially, $C_2$–$C_7$ lower alkenyl is preferred.

The term "aryl" by itself or as a part of (an)other substituent(s) means aromatic carbocyclic group, which includes phenyl, naphthyl and the like. Examples of "optionally substituted aryl" include phenyl, 3,5-dichlorophenyl, 2,4-difluorophenyl, 3,5-difluorophenyl, 3,5-dimethylphenyl, 3,5-dimethoxyphenyl, 2,4,6-trimethylphenyl, 3,5-di-tert-butylphenyl, 4-methoxyphenyl, 4-benzylphenyl, 4-hydroxyphenyl, 3,5-dinitrophenyl, 3-nitrophenyl, 3,5-diaminophenyl, 3-aminophenyl, naphthyl and the like.

The term "arylthio" includes phenylthio or naphthylthio.

The term "heteroaryl" by itself or as a part of (an)other substituent(s) means aromatic 5 to 7 membered heterocyclic group containing at least one hetero atom (N, O, or S), which includes pyridyl (e.g., 4-pyridyl), pyrimidinyl (e.g., 2-pyrimidinyl), pyridazinyl (e.g., 3-pyridazinyl), pyrazinyl (e.g., 2-pyrazinyl), thienyl (e.g., 2-thienyl), quinolyl (e.g., 3-quinolyl), imidazolyl (e.g., 2-imidazolyl), oxazolyl (e.g., 2-oxazolyl), thiazolyl (e.g., 5-thiazolyl) and the like. Especially, pyridyl is preferred.

The term "heteroarylalkyl" includes pyridylmethyl (e.g., 4-pyridylmethyl), pyridylethyl (e.g., 1-(2-pyridyl)ethyl or 2-(2-pyridyl)ethyl), pyridylpropyl (e.g., 3-(2-pyridyl)propyl), thienylmethyl (e.g., 2-thienylmethyl), quinolylmethyl (e.g., 3-quinolylmethyl), imidazolylmethyl (e.g., 2-imidazolylmethyl) and the like.

The term "aralkyl" by itself or as a part of (an)other substituent(s) means arylalkyl, which includes benzyl, phenethyl (e.g., 1-phenethyl), naphthylmethyl, naphthylethyl (e.g., 2-naphthylethyl) and the like.

The term "acyl" by itself or as a part of (an)other substituent(s) means alkylcarbonyl or arylcarbonyl, which includes acetyl, propionyl, pivaloyl, benzoyl and the like.

The term "optionally substituted carbamoyl" includes unsubstituted carbamoyl or mono- or di-substituted carbamoyl, such as carbamoyl, N-methylcarbamoyl, N,N-dimethylcarbamoyl and the like.

The term "alkoxycarbonyl" includes methoxycarbonyl, ethoxycarbonyl and the like.

The term "halogen" means fluoro, chloro, bromo or iodo. Especially, chloro or bromo is preferred.

The term "optionally substituted amino" means unsubstituted amino or mono- or di-substituted amino, which includes amino, methylamino, dimethylamino and the like.

The term "aralkyloxyalkyl" includes benzyloxymethyl, benzyloxyethyl, phenethyloxymethyl (e.g., 1-phenethyloxymethyl) and the like.

The term "aryloxyalkyl" includes phenyloxymethyl, phenyloxyethyl, 3,5-dichlorophenyloxymethyl and the like.

The term "acylalkyloxyalkyl" includes acetylmethyloxymethyl, acetylmethyloxyethyl, propionylethyloxymethyl, benzoylmethyloxymethyl, benzoylethyloxymethyl, benzoylmethyloxyethyl and the like.

The term "acyloxyalkyl" includes acetyloxymethyl, acetyloxyethyl, propionyloxymethyl, benzoyloxymethyl, benzoyloxyethyl and the like.

The term "alkoxycarbonylalkyloxyalkyl" includes methoxycarbonylmethyloxymethyl, methoxycarbonylethyloxymethyl and the like.

The term "alkoxycarbonyloxyalkyl" includes methoxycarbonyloxymethyl, methoxycarbonyloxyethyl and the like.

The term "optionally substituted carbamoylalkyloxyalkyl" includes carbamoylmethyloxymethyl, carbamoylmethyloxyethyl, carbamoylethyloxymethyl, N-methylcarbamoylmethyloxymethyl, N,N-dimethylcarbamoylmethyloxymethyl and the like.

The term "optionally substituted carbamoyloxyalkyl" includes carbamoyloxymethyl, carbamoyloxyethyl, N-methylcarbamoyloxymethyl, N,N-dimethylcarbamoyloxymethyl and the like.

When each group described above is substituted, the substituent refers to, for example alkyl (e.g., methyl, ethyl), halogen (fluoro, chloro, bromo, iodo), acyl (e.g., acetyl, benzoyl), alkenyl (e.g., allyl), cycloalkyl (e.g., cyclopropyl), aralkyl (e.g., benzyl), optionally substituted amino (e.g., methylamino, dimethylamino), hydroxy, oxo, alkoxy (e.g., methoxy, ethoxy), cyano, carboxy, alkoxycarbonyl (e.g., methoxycarbonyl), nitro, acyloxy (e.g., acetyloxy), optionally substituted carbamoyl (e.g., N-methylcarbamoyl), optionally substituted carbamoyloxy (N-ethylcarbamoyloxy) and the like. One or more substituent(s) may be at any substitutable position(s). When the substituent interferes the reaction, a protective group may be introduced before the reaction, and then removed at any suitable step after the reaction.

Examples of the present invention are shown below.

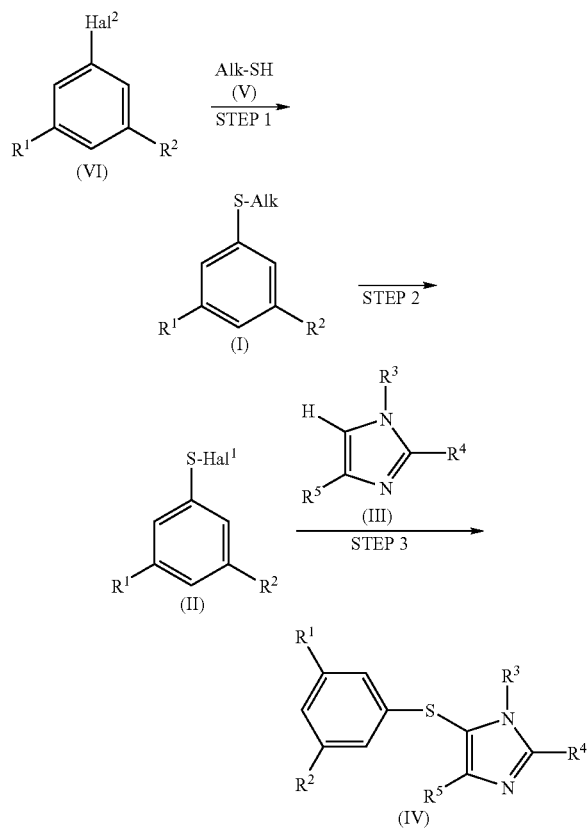

wherein Alk, Hal¹, Hal², R¹, R², R³, R⁴ and R⁵ are as defined above.

(Process 1)

This process is the process for producing the compound of the formula (I), which comprises reacting the compound of the formula (V) with the compound of the formula (VI) in the presence of a base.

The compound of the formula (V) includes commercially available isopropylmercaptan and tert-butylmercaptan. The compound of the formula (VI) can be commercially available or prepared in accordance with general procedure, which includes, for example 1,3,5-trichlorobenzene, 1,3,5-tribromobenzene, 1-bromo-3,5-dichlorobenzene, 1,3-dibromo-5-chlorobenzene, 1-chloro-3,5-dibromobenzene, 1-chloro-3,5-dimethylbenzene, 1-bromo-3,5-dimethoxybenzene, 1,3-dichloro-5-nitrobenzene, 1-chloro-3,5-dicyanobenzene, 1-chloro-3-methyl-5-nitrobenzene, 1-nitro-3,5-dichlorobenzene and the like. Espacially, 1-bromo-3,5-dichlorobenzene or 1,3,5-trichlorobenzene is preferred.

The compound of the formula (V) in gas state or liquid state may be added to an alkaline aqueous solution, to prepare an aqueous solution containing the salt of the compound of the formula (V), or the compound of the formula (V) in gas state or liquid state may directly be added to the reaction mixture prepared with base and water. In this process, the amount of the compound of the formula (V) is usually 0.5 to 5.0 mole equivalents, preferably 1.0 to 1.5 mole equivalents to the compound of the formula (VI). The reaction temperature can be 0 to 200° C., preferably 25 to 140° C.

The base to be used includes alkaline metal hydroxide such as sodium hydroxide, potassium hydroxide and the like; alkaline metal carbonate such as sodium carbonate, potassium carbonate and the like. Especially, sodium hydroxide is preferred. The amount of the base is usually 0.5 to 2.0 mole equivalents, preferably 1.0 to 1.2 mole equivalents to the compound of the formula (V).

The solvent to be used is water, two phase mixed solvent comprising water and non water-miscible organic solvent, or organic solvent. In case of water solvent, the aqueous solution containing the salt of the compound of the formula (V) may be prepared in advance as shown above. Non water-miscible organic solvent includes, is not limited to, cyclohexane, methylcyclohexane, benzene, toluene, xylene, monochlorobenzene, dichlorobenzene and the like. In case of mixed solvent comprising water and non water-miscible organic solvent, the amount of the non water-miscible organic solvent is 0.5 to 5.0 weight equivalents, preferably 1.0 to 2.0 weight equivalents to water. The compound of the formula (VI) itself, for example 1,3,5-trichlorobenzene, may be used as a non water-miscible organic solvent. In this case, the reaction is carried out in two phase-mixed solvent because 1,3,5-trichlorobenzene is non water-miscible organic solvent. The addition of phase transfer catalyst is preferable to perform the reaction smoothly.

The phase transfer catalyst to be used includes quaternary ammonium salt such as tetraethylammoniumbromide, tetraethylammoniumchloride, tetra-n-propylammoniumbromide, tetra-n-propylammoniumchloride, tetra-n-butylammoniumbromide, tetra-n-butylammoniumchloride, tetra-n-pentylammoniumbromide, tetra-n-pentylammoniumchloride, tetra-n-hexylammoniumbromide, tetra-n-hexylammoniumchloride, tetra-n-heptylammoniumbromide, tetra-n-heptylammoniumchloride, tetra-n-octylammoniumbromide, tetra-n-octylammoniumchloride, benzyltriethylammoniumbromide, benzyltriethylammoniumchloride and the like; quaternary phosphonium salt such as tetraethylphosphoniumbromide, tetraethylphosphoniumchloride, tetra-n-propylphosphoniumbromide, tetra-n-propylphosphoniumbromide, tetra-n-butylphosphoniumchloride, tetra-n-butylphosphoniumchloride, tetra-n-pentylphosphoniumbromide, tetra-n-pentylphosphoniumchloride, tetra-n-hexylphosphoniumbromide, tetra-n-hexylphosphoniumchloride, tetra-n-heptylphosphoniumbromide, tetra-n-heptylphosphoniumchloride, tetra-n-octylphosphoniumbromide, tetra-n-octylphosphoniumchloride, tetraphenylphosphoniumbromide, tetraphenylphosphoniumchloride and the like. In particullar, preferred is quaternary ammonium salt such as tetra-n-butylammoniumbromide, tetra-n-butylammoniumchloride and the like. The amount of the catalyst is usually 0.01 to 1.0 mole equivalents to the compound of the formula (VI). These catalyst can be used by itself or as the combination of two or more quaternary ammonium salts, two or more quaternary phosphonium salts, or quaternary ammonium salts and quaternary phosphonium salts.

In case of organic solvent to be used by itself, can be used the polar solvent such as hexamethylphosphoroustriamide, dimethylformamide, dimethylsulfoxide, N-methyl-2-pyrrolidone, N,N-dimethylacetamide and the like. Especially, hexamethylphosphoroustriamide is preferred.

(Process 2)

This process is the process for producing the compound of the formula (II), which comprises allowing the halogenating agent to react with the compound of the formula (I).

The halogenating agent includes chlorinating agent such as chlorine, sulfuryl chloride, N-chlorosuccinimide and the like, brominating agent such as bromine, N-bromosuccinimide and the like or iodine. Especially, chlorine or bromine is preferred. The amount of the halogenating agent is 1.0 to 10 mole equivalents, preferably 3.0 to 5.0 mole equivalent to the compound of the formula (I).

The solvent to be used includes, is not limited to, hydrocarbon such as hexane, cyclohexane, heptane and the like, halogenated hydrocarbon such as dichloroethane, dichloromethane, chloroform, trichloromethane, carbon tetrachloride and the like, aromatic hydrocarbon such as benzene, toluene, xylene, chlorobenzene, dichlorobenzene, trichlorobenzene and the like. When the solvent is used, the amount of the solvent is, is not limited to, 1 to 100 weight equivalents to the compound of the formula (I). The reaction mixture is −10 to 50° C., preferably 0 to 20° C.

(Process 3)

This process is the process for producing the compound of the formula (IV) which comprises reacting the compound of the formula (II) with the compound of the formula (III).

Some of the compounds of the formula (III) have been known, which can be prepared in accordance with the process described in WO96/10019 and JP-A 6-116242. The compound of the formula (III) to be used in the present invention includes 2-benzyloxymethyl-4-isopropyl-1H-imidazole, 2-benzyloxymethyl-4-isopropyl-1-(pyridin-4-yl)methyl-1H-imidazole, 2-acetyloxymethyl-4-isopropyl-1-(pyridin-4-yl)methyl-1H-imidazole, 2-benzoyloxymethyl-4-isopropyl-1-(pyridin-4-yl)methyl-1H-imidazole, 2-methoxycarbonyloxymethyl-4-isopropyl-1-(pyridin-4-yl)methyl-1H-imidazole, 2-carbamoyloxymethyl-4-isopropyl-1-(pyridin-4-yl)methyl-1H-imidazole and the like. Especially, 2-carbamoyloxymethyl-4-isopropyl-1-(pyridin-4-yl)methyl-1H-imidazole is preferred.

The base to be used includes triethylamine, N-methylmorpholine, pyridine, N,N-dimethylaniline, N,N-diisopropyl-N-ethylamine, butyl lithium, diazabicycloundecene and the like. The solvent to be used includes acetonitrile, toluene, methylene chloride, chloroform, dimethylformamide, nitromethane, benzene, tetrahydrofuran and the like.

In this process, the amount of base is 0.1 to 3.0 mole equivalents, preferably 1.0 to 2.0 mole equivalents to the compound of the formula (III). The amount of the compound of the formula (II) is 1.0 to 3.0 mole equivalents, preferably 1.0 to 2.0 mole equivalent to the compound of the formula (II). The reaction temperature is −30 to 60° C., preferably 0 to 10° C. To the compound of the formula (II) may be added under stirring the compound of the formula (III), and vice versa. The base may mixed with the compound of the formula (III) in advance, or may be added at the end.

The following examples are provided to further illustrate the present invention and are not to be construed as limiting the scope thereof.

The meanings of the following abbreviations in the examples are shown below.

| Me | methyl |
| Pr$^i$ | isopropyl |
| Bu$^t$ | tert-butyl |
| Bn | benzyl |
| Ph | phenyl |
| HMPT | hexamethylphosphorous triamide |
| TEA | triethylamine |
| DMF | dimethylformamide |

EXAMPLE 1

3,5-Dichlorophenyl-isopropylsulfide (2)

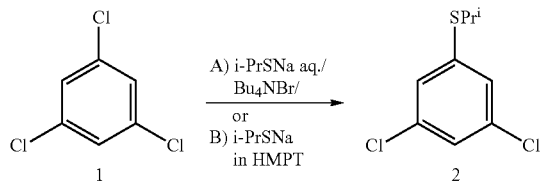

Method A

To a solution of 4N sodium hydroxide (0.8 ml) was added isopropylmercaptan (0.33 ml). The mixture was stirred for 10 minutes at room temperature. 1,3,5-Trichlorobenzene(1) (1.8 g, 10 mmol) and tetra n-butylammoniumbromide (322 mg, 1 mmol) were added thereto. The reaction mixture was refluxed under vigorous stirring at 140° C. for 5.5 hours. The reaction mixture was poured into ice-water, extracted with ethylacetate, washed with water, dried over sodium sulphate, filtrated and concentrated under reduced pressure. The obtained residue was chromatographed twice on silica gel (SiO$_2$ 18 g, elution: n-hexane) to yield the objective (2) (566 mg). Yield 85%.

IR(film) 1555, 1400, 1375, 1360, 1155 cm$^{-1}$.

$^1$H-NMR(CDCl$_3$, 200 MHz) δ: 1.32(6H, d, J=6.4 Hz), 3.42(1H, sept, J=6.4 Hz), 7.15–7.25(3H, m).

Method B

To a solution of sodium hydride (120 mg, 3 mmol, in oil, 60% cont.) in anhydrous methanol (5 ml) was added isopropylmercaptan (0.335 ml). The mixture was stirred for 10 minutes at room temperature. The reaction mixture was concentrated dryness under reduced pressure and dried up. The obtained sodium isopropylmercaptan was dissolved in HMPT (2 ml). 1,3,5-trichlorobenzene (1) (1.8 g, 10 mmol) was added thereto. The mixture was stirred for 2.5 hours at 80° C. The reaction mixture poured into ice-water. The mixture was extracted with ethylacetate, washed with water, dried over sodium sulphate, filtrated and concentrated under reduced pressure. The obtained residue was chromatographed twice on silica gel (SiO$_2$ 25 g, elution: n-hexane) to yield the objective (2) (475 mg). Yield 71%.

EXAMPLE 2

2-Benzyloxymethyl-5-(3,5-dichlorophenylthio)-4-isopropyl-1-(pyridin-4-yl)methyl-1H-imidazole (6)

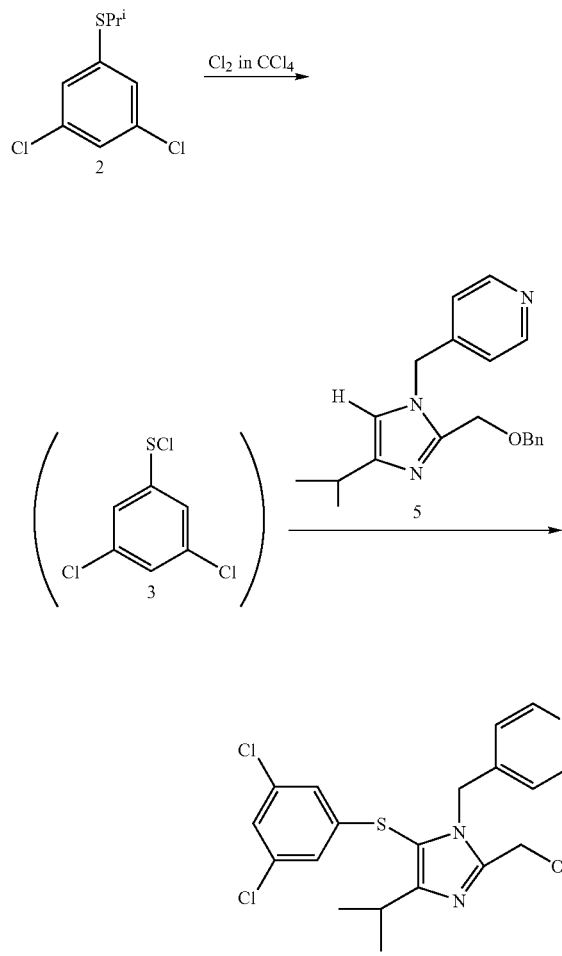

To a solution of the compound (2) (221 mg, 1 mmol) prepared in Example 1 in carbon tetrachloride (1 ml) was added under stirring and ice-cooling chlorine (0.7 mol/l in carbon tetrachloride, 5.6 ml). The reaction mixture was stirred at the same temperature for 3.5 hours. The solvent was removed under reduced pressure, and excess of chlorine was removed too. The concentrated residue was dissolved in toluene (5 ml). The compound (5) (prepared in accordance with Reference Example 1 of WO96/10019) (321 mg) and N-methyl morpholine (0.24 ml) were added under ice-cooling thereto. The mixture was stirred at the same temperature for 2 hours. The reaction mixture was allowed to stand over night at room temperature. The mixture was poured into ice-water containing sodium bicarbonate, extracted with ethylacetate, washed with water, dried over sodium sulphate, filtrated and concentrated under reduced pressure. The obtained residue was chromatographed on silica gel (SiO$_2$ 15 g, elution: toluene-ethyl acetate 1:1 to ethyl acetate) to yield the objective (6) (186 mg) as first fraction and the non-reacted compound (5) (162 mg) as second fraction.

Yield of the compound (6) to the compound (2): 38%.

EXAMPLE 3

3,5-Dichlorophenyl-tert-butylsulfide (4)

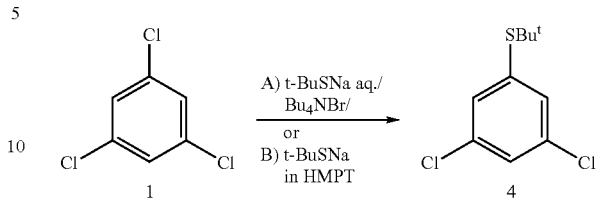

Method A

To a solution of 4N sodium hydroxide (0.8 ml) was added tert-butylmercaptan (0.406 ml). The mixture was stirred for 15 minutes at room temperature. Tetra n-butylammonium bromide (322 mg, 1 mmol) and 1,3,5-trichlorobenzene (1) (1.8 g, 10 mmol) were added thereto. The reaction mixture was refluxed at 140° C. for 6.5 hours. The reaction mixture was poured into ice-water, extracted with ethylacetate, washed with water, dried over sodium sulphate, filtrated and concentrated under reduced pressure. The obtained residue was chromatographed twice on silica gel (SiO$_2$ 15 g, elution: n-hexane) to yield the objective (4) (138 mg). Yield 19%.

IR(film) 1555, 1400, 1380, 1360 cm$^{-1}$. $^1$H-NMR(CDCl$_3$, 200 MHz) δ: 1.31(9H, S), 7.34–7.44(3H, m)

Method B

To a solution of sodium hydroxide (120 mg, 3 mmol, in oil, 60% cont.) in anhydrous methanol (5 ml) was added tert-butyl mercaptan (0.406 ml). The mixture was stirred for 20 minutes at room temperature. The reaction mixture was concentrated dryness under reduced pressure. The obtained sodium isopropylmercaptan was dissolved in HMPT (2 ml). 1,3,5-trichlorobenzene (1) (1.8 g, 10 mmol) was added thereto. The mixture was stirred for 2 hours and 50 minutes at 80° C. The reaction mixture was poured into ice-water. The mixture was extracted with ethylacetate, washed with water, dried over sodium sulphate, filtrated and concentrated under reduced pressure. The obtained residue was chromatographed twice on silica gel (SiO$_2$ 15 g, elution: n-hexane) to yield the objective (4) (293 mg). Yield 41%.

EXAMPLE 4

2-Benzyloxymethyl-5-(3,5-dichlorophenylthio)-4-isopropyl-1-(pyridin-4-yl)methyl-1H-imidazole (6)

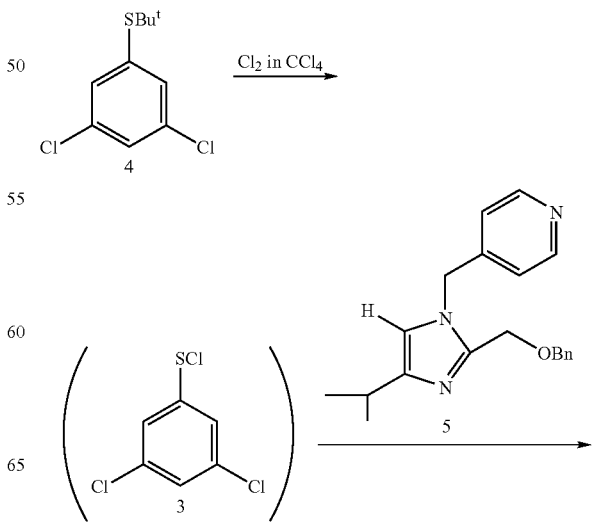

15

-continued

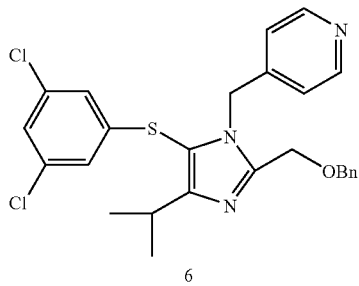

6

To a solution of the compound (4) (235 mg, 1 mmol) prepared in Example 3 in carbon tetrachloride (1 ml) was added under ice-cooling chlorine (0.7 mol/l in carbon tetrachloride, 4.2 ml). The reaction mixture was stirred at the same temperature for 1.5 hours. The solvent was removed under reduced pressure, and excess of chlorine was removed too. The concentrated residue was dissolved in toluene (5 ml). The compound (5) (prepared in accordance with Reference Example 1 of WO96/10019) (321 mg, 1 mmol) and N-methyl morpholine (0.24 ml) were added under ice-cooling thereto. The mixture was stirred at the same temperature for 1 hour. The reaction mixture was allowed to stand over night at room temperature. The mixture was poured into ice-water containing sodium bicarbonate, extracted with ethylacetate, washed with water, dried over sodium sulphate and concentrated under reduced pressure. The obtained residue was chromatographed on silica gel (SiO₂ 15 g, elution: toluene-ethylacetate 1:1 to ethylacetate) to yield the objective (6) (233 mg) as first fraction and the non-reacted compound (5) (143 mg) as second fraction.

Yield of the compound (6) to the compound (4): 46%.

EXAMPLE 5

2-Benzyloxymethyl-5-(3,5-dichlorophenylthio)-4-isopropyl-1H-imidazole (8)

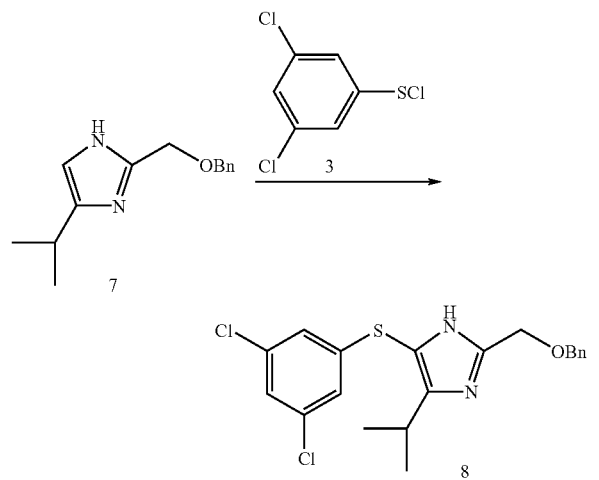

2-Benzyloxymethyl-4-isopropyl-1H-imidazole (7) (550 mg, 2.4 mmol), described as Reference Example 1 of WO 96/10019 was dissolved in a mixture of triethylamine 360 mg (3.6 mmol) and acetonitrile 4 ml. To the solution was added 3,5-dichlorobenzenesulfenyl chloride (3) 930 mg (4.4 mmol) at room temperature. The mixture was stirred for 30 minutes at room temperature and water (15 ml) and toluene (15 ml) were added thereto. The toluene layer was separated, washed with water 10 ml twice, and concentrated under reduced pressure. The obtained yellow oil was crystallized with diisopropyl ether 10 ml, filtered, and dried to yield the objective (8) 800 mg as a pale yellow crystal. Yield 82%.

¹H-NMR (CDCl₃-TMS) δ ppm: 1.22 (d, J=7.2 Hz, 6H), 3.64 (sept, 1H), 4.62 (s, 2H), 4.67 (s, 2H), 6.92 (bs, 2H), 7.07 (bs, 1H), 7.36 (s, 5H), 9.20 (b, 1H).

EXAMPLE 6

2-Benzyloxymethyl-5-(3,5-dichlorophenylthio)-4-isopropyl-1-(pyridin-4-yl)methyl-1H-imidazole (6)

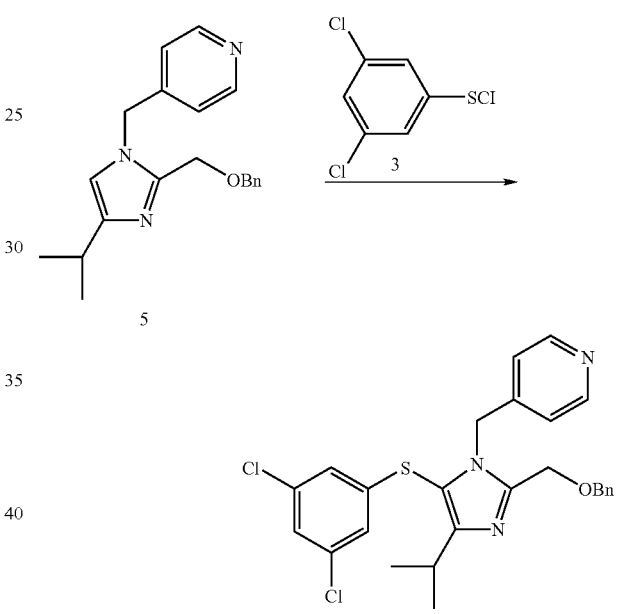

2-Benzyloxymethyl-4-isopropyl-1-(pyridin-4-yl)-1H-imidazole (5) (10.0 g, 31.1 mmol) was dissolved in toluene (50 ml). The solution was added dropwise to a solution of 3,5-dichlorobenzenesulfenyl chloride (3) (8.0 g, 37.05 mmol) in toluene (24.7 g) under ice-cooling for 30 minutes. To the mixture was added dropwise triethylamine (3.5 g, 34.6 mmol) under ice-cooling for 1 hour and the mixture was stirred at the same temperature for 1.5 hours. To the mixture was added water (25 ml) and toluene layer was separated. The toluene layer was washed with water (25 ml) and each aqueous layer was extracted with toluene (10 ml). The toluene layer was collected, concentrated under reduced pressure to give oily product, which was crystallized with diisopropyl ether 50 ml, filtered and dried to yield the objective (6) (12.6 g) as a pale yellow crystal. Yield 81.3%.

¹H-NMR (CDCl₃) δ ppm: 1.30 (d, J=7.2 Hz, 6H), 3.08–3.22 (m, 1H), 4.52 (s, 2H), 4.62 (s, 2H) 5.16 (s, 2H), 6.65 (d, J=1.8 Hz, 2H), 6.79 (d, J=6.0 Hz, 2H), 7.03 (t, J=1.8 Hz, 1H), 7.18–7.36 (m, 5H), 8.38 (d, J=6.0 Hz, 2H).

Reference Example 1

2-Acetyloxymethyl-4-isopropyl-1-(pyridin-4-yl)methyl-1H-imidazole (10a)

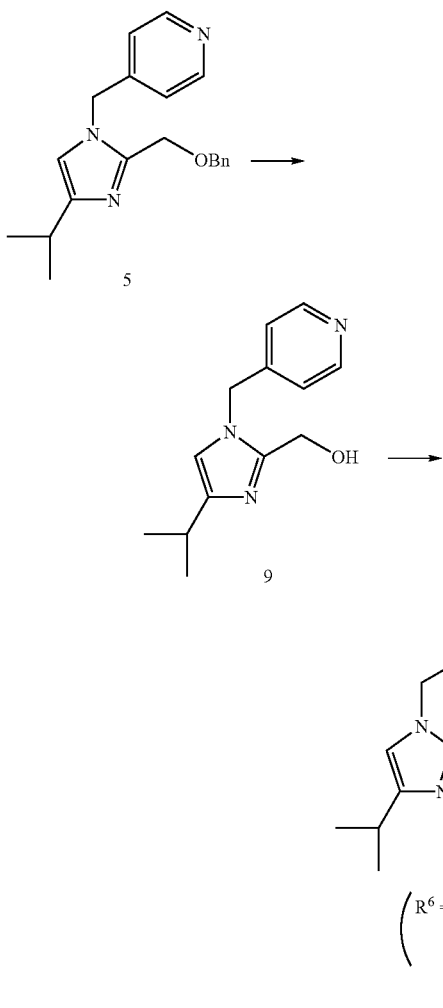

The compound (5) (20.0 g, 62.2 mmol) was suspended in 35% aqueous hydrochloric acid (100 ml). The solution was heated at 85° C. and stirred for 1 hour. The reaction mixture was cooled down to room temperature and water (100 ml) and toluene (44 ml) were added thereto with stirring. The aqueous layer was separated and neutralized with 30% aqueous sodium hydroxide, to which ethyl acetate (30 ml) was added with stirring. The obtained slurry was filtered, washed with cold water and dried to yield 2-hydroxymethyl-4-isopropyl-1-(pyridin-4-yl)-1H-imidazole (9) (11.7 g). Yield 81.4%.

$^1$H-NMR (CDCl$_3$) δ ppm: 1.16 (d, J=7.0 Hz, 6H), 2.68–2.89 (m, 1H), 4.59 (s, 2H), 5.23 (s, 2H), 6.51 (s, 1H), 7.03 (d, J=6.0 Hz, 2H), 8.55 (d, J=6.0 Hz, 2H).

To a solution of the above-obtained hydroxy compound (9) (3.49 g, 15 mmol) and triethylamine (1.83 g, 18 mmol) in dichloromethane (35 ml), was added dropwise acetylchloride (1.32 g, 17 mmol) under ice-cooling. The mixture was stirred for 1 hour under ice-cooling. Water was added thereto. The dichloromethane layer was evaporated and the residue was purified by column chromatography on silica gel (elution ethyl acetate:methanol=10:1) to yield the objective (10a) (3.34 g). Yield 81.1%.

$^1$H-NMR (CDCl$_3$) δ ppm: 1.26 (d, J=7.0 Hz, 6H), 1.85 (s, 3H), 2.88–3.05 (m, 1H), 5.11 (s, 2H), 5.15 (s, 2H), 6.64 (s, 1H), 6.95 (d, J=6.0 Hz, 2H), 8.59 (d, J=6.0 Hz, 2H).

In accordance with the same method described above, the above-obtained hydroxy compound (9) (1.16 g, 5 mmol), dichloromethane (12 ml), triethylamine (0.86 g, 8.5 mmol) and benzoylchloride (1.16 g, 8.3 mmol) were reacted to yield the objective (10b) (1.65 g). Yield 93.2%. (elution: ethyl acetate)

$^1$H-NMR (CDCl$_3$) δ ppm: 1.34 (d, J=7.0 Hz, 6H), 2.90–3.10 (m, 1H), 5.29 (s, 2H), 5.45 (s, 2H), 6.74 (s, 1H), 6.99 (d, J=6.0 Hz, 2H), 7.30–7.90 (m, 5H), 8.55 (d, J=6.0 Hz, 2H).

In accordance with the same method described above, the above-obtained hydroxy compound (9) (1.16 g, 5 mmol), dichloromethane (12 ml), triethylamine (0.76 g, 7.5 mmol) and methyl chloroformate (0.70 g, 7.4 mmol) were reacted to yield the objective (10c) (0.40 g), methoxycarbonyloxy derivative. Yield 27.6%.

$^1$H-NMR (CDCl$_3$) δ ppm: 1.25 (d, J=7.0 Hz, 6H), 2.80–3.00 (m, 1H), 3.70 (s, 3H), 5.17 (s, 2H), 5.18 (s, 2H), 6.64 (s, 1H), 6.97 (d, J=6.0 Hz, 2H), 8.59 (d, J=6.0 Hz, 2H).

EXAMPLE 7

2-Acetyloxymethyl-5-(3,5-dichlorophenylthio)-4-isopropyl-1-(pyridin-4-yl)methyl-1H-imidazole (11)

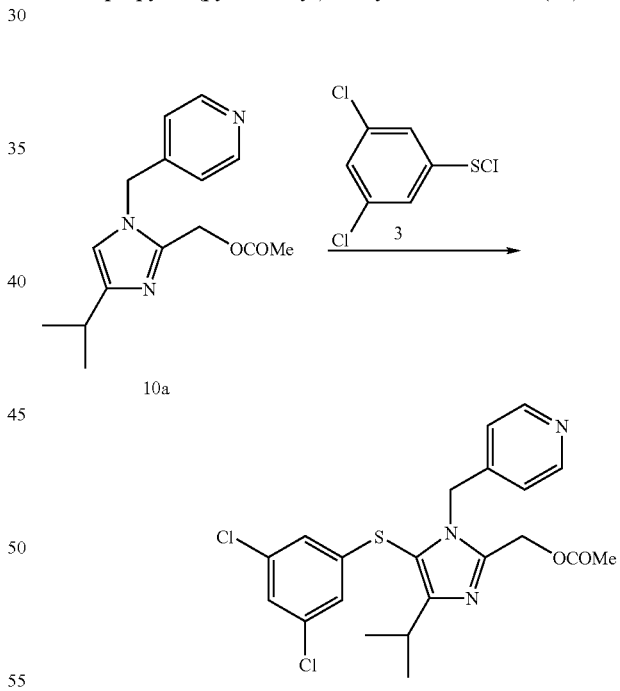

To a solution of the compound (3) (0.97 g, 4.5 mmol) in toluene (1.88 g) was added dropwise a solution of the compound (10a) (0.87 g, 3.2 mmol) in acetonitrile (4 ml) under ice-cooling for 30 minutes. A solution of triethylamine (0.46 g, 4.5 mmol) in acetonitrile (0.5 ml) was added dropwise thereto for 15 minutes, and the mixture was stirred under ice-cooling for 2 hours. The reaction mixture was concentrated under reduced pressure and extracted with ethyl acetate. The extract was washed with water, concentrated under reduced pressure and purified by column chromatography on silica gel (elution ethyl acetate) to yield the objective (11) (1.17 g) as a crystal. Yield 82%. Mp 133–135° C.

¹H-NMR (CDCl₃-TMS) δ ppm: 1.31 (d, J=6.0 Hz, 6H), 1.85 (s, 3H), 3.18–3.30 (m, 1H), 5.18 (s, 2H), 5.19 (s, 2H) 6.69 (d, J=2.0 Hz, 2H), 6.78 (d, J=6.0 Hz, 2H), 7.05 (d, J=2.0 Hz, 1H), 8.45 (d, J=6.0 Hz, 2H).

Reference Example 2

2-Hydroxymethyl-5-(3,5-dichlorophenylthio)-4-isopropyl-1-(pyridin-4-yl)methyl-1H-imidazole (12)

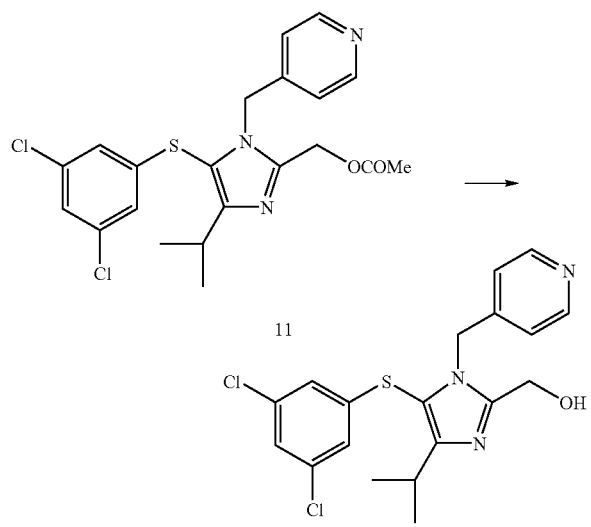

To a suspension of the compound (11) (0.35 g, 0.77 mmol) obtained in Example 7 in ethanol (3.5 ml) was added 1N aqueous sodium hydroxide (0.82 ml) under ice-cooling. The reaction mixture was stirred for 30 minutes, concentrated under reduced pressure and extracted with ethyl acetate. The extract was washed with water and concentrated under reduced pressure to yield the objective (12) (0.31 g). Yield 96.9%.

Reference Example 3

2-Carbamoyloxymethyl-4-isopropyl-1-(pyridin-4-yl)methyl-1H-imidazole (13)

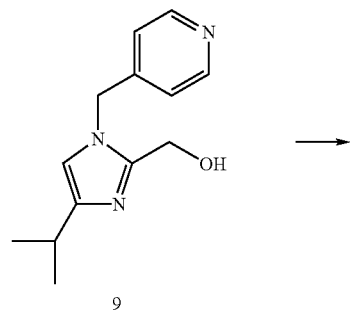

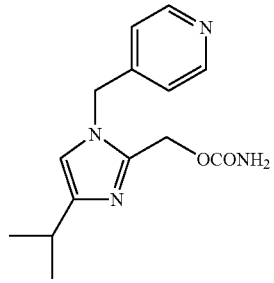

The hydroxy compound (9) (15.0 g, 64.9 mmol) was suspended in acetonitrile (150 ml). To the suspension was added dropwise anhydrous hydrochloric acid (5.2 g, 142.5 mmol) in ethyl acetate (42 ml) at room temperature. The mixture was cooled down to 0° C. under nitrogen atmosphere, and chlorosulfonyl isocyanate (22.0 g, 155.4 mmol) was added dropwise thereto under cooling for 45 minutes. The reaction mixture was stirred at the same temperature for 1 hour, and water (13.5 ml) and 35% aqueous hydrochloric acid (13.5 ml) were added thereto. The mixture was stirred at 45° C. for 1 hour, cooled down to room temperature, and neutralized by 20% aqueous sodium carbonate. The mixture was kept stationary and separated. The organic layer was washed with water, and the aqueous layer was extracted with ethyl acetate. The organic layer was collected and concentrated dryness. To the residue was added diisopropyl ether (80 ml), and the solution was stirred for 1 hour at room temperature. The obtained slurry was filtered, washed with diisopropyl ether and dried to yield the objective (13) (14.8 g). Yield 83.2%.

¹H-NMR (CDCl₃-TMS) δ ppm: 1.25 (d, J=7.0 Hz, 6H), 2.80–3.00 (m, 1H), 4.95 (bs, 2H), 5.10 (s, 2H), 5.20 (s, 2H), 6.63 (s, 1H), 6.97 (d, J=5.2 Hz, 2H), 8.57 (d, J=5.0 Hz, 2H).

EXAMPLE 8

2-Carbamoyloxymethyl-5-(3,5-dichlorophenylthio)-4-isopropyl-1-(pyridin-4-yl)methyl-1H-imidazole (14)

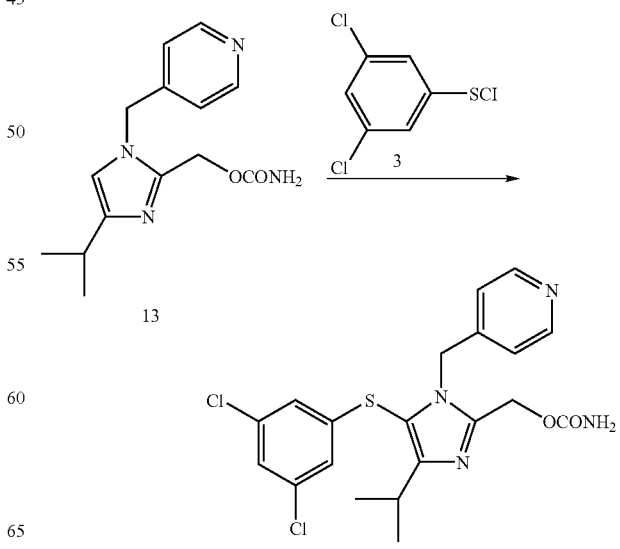

The compound (13) (250 mg, 0.91 mmol) was dissolved in N,N-dimethylformamide (4 ml). The solution was cooled down to −30° C. under nitrogen atmosphere. To the solution were added, alternately each four time, a solution of the compound (3) (77 mg, 0.36 mmol) in toluene (150 mg) and a solution of triethylamine (36 mg, 0.36 mg) in toluene (150 mg), and additionally added a solution of the compound (3) (77 mg, 0.36 mmol) in toluene (150 mg). The reaction mixture was stirred at −30° C. for 30 minutes, and ethyl acetate and aqueous sodium hydrogen carbonate were added thereto. The objective (14) was extracted into the ethyl acetate layer. Diluted aqueous hydrochloric acid was added to the ethyl acetate layer to transfer the objective compound into the aqueous layer. The aqueous solution was neutralized by aqueous sodium hydrogen carbonate and extracted with ethyl acetate. The extract was dried over anhydrous sodium sulfate and concentrated under reduced pressure to give oily residue. The oily residue was dissolved in methanol (0.9 ml), and water (0.7 ml) was added dropwise thereto for 1–2 minutes at room temperature for crystallization. The suspension was stirred for 30 minutes at room temperature, additionally for 30 minutes under ice-cooling, filtered, washed with 50% aqueous methanol, and dried to yield the objective (14) (250 mg) as a white crystal. Yield 61%.

mp88° C. (dec)

$^1$H-NMR (CDCl$_3$-TMS) δ ppm: 1.32 (d, J=6.9 Hz, 6H), 3.17 (sept, 1H), 4.53 (b, 2H), 5.21 (s, 2H), 5.27 (s, 2H), 6.69 (d, J=1.6 Hz, 2H), 6.82 (d, J=5.2 Hz, 2H), 7.06 (t, J=1.6 Hz, 1H), 8.46 (b, 2H). Element analysis (C$_{20}$H$_{20}$Cl$_2$N$_4$O$_2$S 0.5H$_2$O) Calcd. (%):C, 52.16; H, 4.61; N, 12.17; S, 6.96; Cl, 15.42. Found.(%):C, 52.45; H, 4.72; N, 11.73; S, 7.08; Cl, 14.81. 2HCl salt of the compound (14):mp 214–222° C. (dec)

Reference Example 4

2,2-Dichloro-3-methylbutylaldehyde (16)

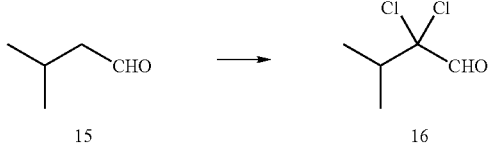

To a mixture of isovalelaldehyde (15) (192 g, 2.23 mol) and N,N-dimethylformamide (230 ml) was introduced chlorine (316 g, 4.46 mol) under 60° C. The mixture was cooled down, mixed with water (384 ml) and separated. The organic layer was washed with aqueous sodium hydrogen carbonate (350 g), and each aqueous layer was extracted with toluene (115 ml). The organic layer was collected to yield a solution of the objective (16) in the toluene (440 g). Yield 75%.

$^1$H-NMR (CDCl$_3$-TMS) δ ppm: 1.15 (d, J=6.6 Hz, 6H), 2.56 (sept, J=6.6 Hz, 1H), 9.24 (s, 1H).

1,4-Dibenzyloxy-2-butene (18)

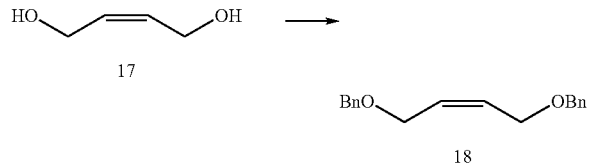

To 48% aqueous sodium hydroxide (127.8 g) was added tetra-n-butylammonium bromide (3.3 g, 10 mmol). The mixture was heated to 60° C. To the mixture was added 2-butene-1,4-diol (17) (30.0 g, 340 mmol), to which was added dropwise benzyl chloride (94.8 g, 743 mmol) at 80±15° C. The mixture was stirred at the same temperature for 2 hours. The reaction mixture was cooled down, and separated after the addition of water (90 ml). To the organic layer was added sulfuric acidic brine. The solution was neutralized by aqueous sodium hydrogen carbonate, separated, mixed with ethyl acetate and concentrated under reduced pressure to yield the objective (18) (104.5 g, quantitative) as an oil residue.

$^1$H-NMR (CDCl$_3$-TMS) δ ppm: 4.05 (d, J=3.8 Hz, 2H), 4.48 (s, 2H), 5.78 (m, 2H), 7.31 (m, 10H).

Benzyloxyacetoaldehyde (19)

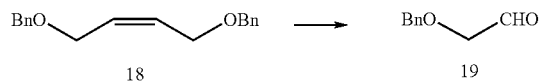

1,4-Dibenzyloxy-2-butene (18) (104.5 g, 340 mmol) obtained above was dissolved in methanol (1458 ml). The solution was cooled down to −60° C. under nitrogen atmosphere. Ozone was introduced thereto at about −60° C. until the starting material disappeared, and then the excess amount of ozone gas was removed by bubbling nitrogen gas. To the solution was added dropwise a solution of triphenylphosphine (107.2 g, 409 mmol) in ethyl acetate (550 ml) at −60° C. to reduce the reaction intermediate. The reaction mixture was warmed to room temperature, and concentrated under reduced pressure to yield an oily mixture of phosphorous compound and the objective (19) (321.6 g, quantitative).

2-Benzyloxymethyl-4-isopropyl-1H-imidazole (7)

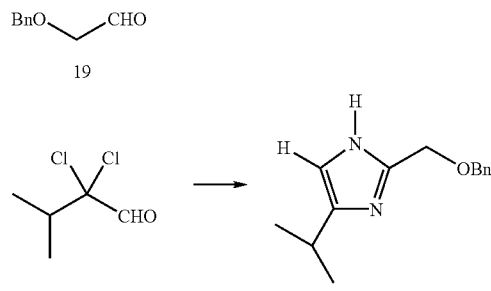

The oil residue of the benzyloxy acetaldehyde (19) (268 g, approximately 0.57 mol) obtained in above (II) and the extract of 2,2-dichloro-3-methylbutylaldehyde (16) (183 g, approximately 0.70 mol) obtained in above (I) were mixed with acetonitrile (276 ml). 25% aqueous ammonia (692 g, 10.2 mol) was added thereto. The mixture was stirred at 45° C. for 8 hours, extracted with toluene 213 ml and separated to yield the extract of the objective (7) (725 g). Yield 70%. The compound (7) can be isolated as crystal from n-hexane.

$^1$H-NMR (CDCl$_3$-TMS) δ ppm: 1.23 (d, J=6.8 Hz, 6H), 2.88 (sept, J=6.8 Hz, 1H), 4.51 (s, 2H), 4.58 (s, 2H), 6.65 (d, J=1.0 Hz, 1H), 7.1–7.4 (m, 5H).

4-Chloromethylpyridine hydrochloride (21)

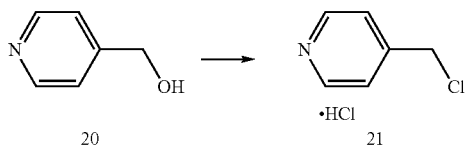

4-Hydroxymethylpyridine (20) (54.4 g, 0.50 mol) was dissolved in acetonitrile 202 ml. The solution was added dropwise to a mixture of thionyl chloride (65.3 g, 0.55 mol) and acetonitrile (109 ml) under 50° C. The mixture was stirred at the same temperature for 1 hour, then cooled to room temperature to yield a slurry (quantitative) of the objective (21).

$^1$H-NMR (DMSO-TMS) δ ppm: 5.09 (s, 2H), 8.09 (d, J=6.6 Hz, 2H), 8.94 (d, J=6.6 Hz, 2H).

2-Benzyloxymethyl-4-isopropyl-1-(pyridin-4-yl) methyl-1H-imidazole 2 nitrate (22)

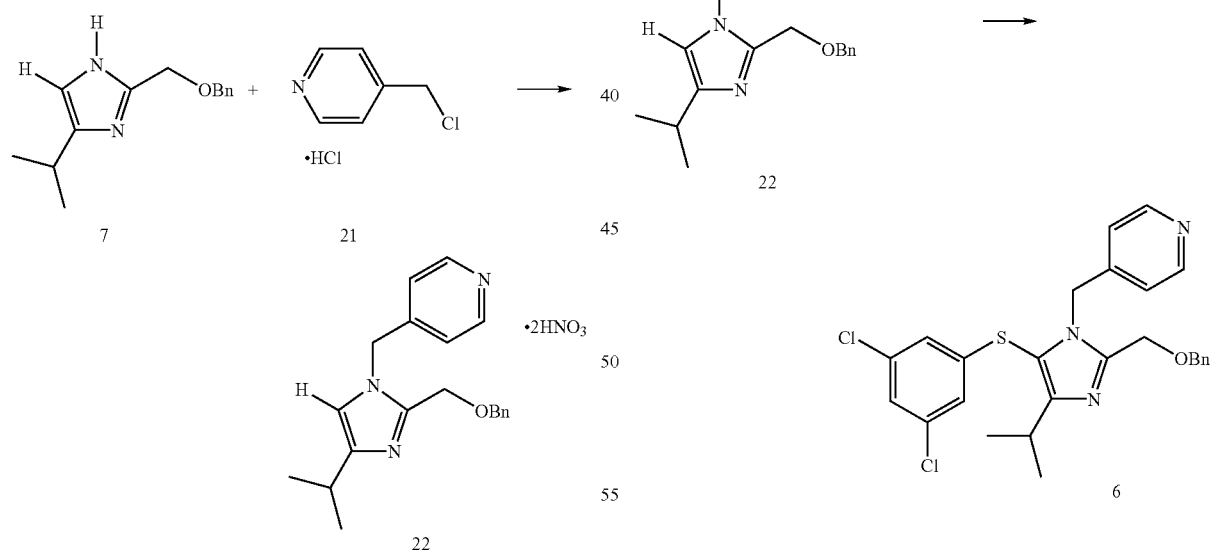

The extract of 2-benzyloxymethyl-4-isopropyl-1H-imidazole (7) (725 g, approximately 0.40 mol) obtained in above (III) was neutralized by aqueous sulfuric acid, mixed with the slurry of 4-chloromethylpyridine hydrochloride (21) (approximately 0.50 mol) obtained in above (IV) and water, and then alkalified by aqueous sodium hydroxide. The mixture was separated, the aqueous layer was extracted with toluene (65 ml), and the organic layer was collected. The organic layer was concentrated to about 830 ml, mixed with sodium hydroxide (62.6 g), and stirred at about 40° C. for 5 hours. The reaction mixture was mixed with water (226 ml) and separated. The aqueous layer was extracted with toluene (65 ml), and the organic layer was collected. The organic layer was mixed with 20% aqueous sulfuric acid (348 g) and the aqueous layer containing the objective compound was separated. The organic layer was extracted with water (65 ml), and the aqueous layer was collected. The aqueous layer was mixed with 20% aqueous sodium hydroxide (282 g) and extracted with ethyl acetate (130 ml). The organic layer was washed with brine, and each aqueous layer was extracted with ethyl acetate (65 ml). The organic layer was collected, concentrated dryness under reduced pressure. The residue was mixed with ethyl acetate (523 ml) and methanol (131 ml), crystallized by concentrated sulfuric acid (82.9 g, 0.89 mol), filtered, and dried to yield the objective (22) (161.3 g) as a pale yellow crystal. Yield 90%. mp 155° C. (dec).

The free compound of the objective (22) can be isolated as crystal by diisopropyl ether.

$^1$H-NMR (CD$_3$OD-TMS) δ ppm: 1.34 (d, J=7.0 Hz, 6H), 3.08 (sept, J=7.0 Hz, 1H), 4.86 (s, 2H), 4.89 (s, 2H), 5.78 (s, 2H), 7.16 (m, 2H), 7.28 (m, 2H), 7.49 (d, J=1.0 Hz, 1H), 7.74 (d, J=6.8 Hz, 2H), 8.67 (d, J=6.8 Hz, 2H).

2-Benzyloxymethyl-5-(3,5-dichlorophenylthio)-4-isopropyl-1-(pyridin-4-yl)methyl-1H-imidazole (6)

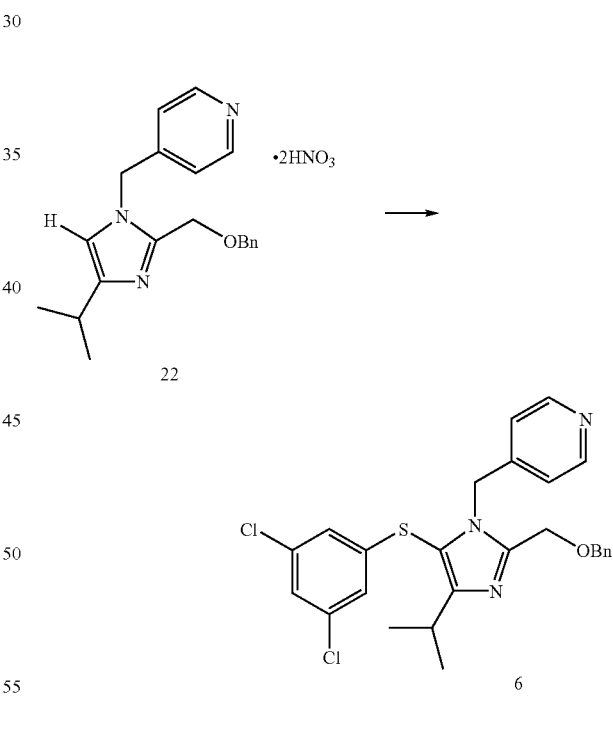

2-Benzyloxymethyl-4-isopropyl-1-(pyridin-4-yl)-1H-imidazole 2 nitrate (22) (13.9 g, 31 mmol) was suspended in toluene (50 ml) and water (12 ml). The suspension was neutralized by 30% aqueous sodium hydroxide. The toluene layer was washed with water (40 ml) and concentrated dryness. The residue was dissolved in toluene (50 ml). The solution was added dropwise to a solution of 3,5-dichlorobenzenesulfenylchloride (3) (7.9 g, 37 mmol) in toluene (24.7 g) under ice-cooling. To the mixture was added dropwise triethylamine (3.5 g, 34 mmol) under ice-cooling for 1 hour. The mixture was stirred at the same temperature for 2.5 hours and mixed with water (25 ml). The toluene layer was separated and washed with water (25 ml), and the aqueous layer was re-extracted with toluene (10 ml). The toluene layer was collected and concentrated under reduced pressure. The oily residue was crystallized by slowly adding diisopropyl ether (50 ml), filtered, and dried to yield the objective (6) (13.0 g) as a pale yellow crystal. Yield 84%.

$^1$H-NMR (CDCl$_3$) δ ppm: 1.30 (d, J=7.2 Hz, 6H), 3.08–3.22 (m, 1H), 4.52 (s, 2H), 4.62 (s, 2H) 5.16 (s, 2H), 6.65 (d, J=1.8 Hz, 2H), 6.79 (d, J=6.0 Hz, 2H), 7.03 (t, J=1.8 Hz, 1H), 7.18–7.36 (m, 5H), 8.38 (d, J=6.0 Hz, 2H).

2-Hydroxymethyl-5-(3,5-dichlorophenylthio)-4-isopropyl-1-(pyridin-4-yl)methyl-1H-imidazole (12)

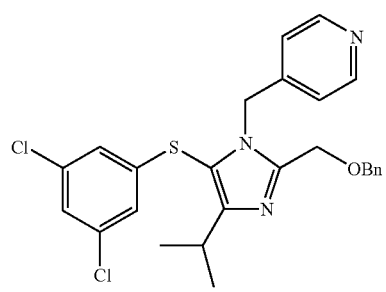

6

To the compound (6) was added concentrated aqueous hydrochloric acid (50 ml). The mixture was heated at 90° C. for 2 hours and then cooled down. To the mixture were added water (50 ml) and toluene (20 ml). The aqueous layer was separated and neutralized by 30% aqueous sodium hydroxide. The compound (12) was extracted with ethyl acetate (50 ml), and the ethyl acetate layer was washed with water (30 ml). Each aqueous layer was extracted with ethyl acetate (20 ml). The ethyl acetate layer was collected and concentrated under reduced pressure to yield oily residue. To the oily residue was slowly added diisopropyl ether (50 ml) for crystallization. The obtained slurry was stirred at room temperature for 30 minutes, filtered, washed with diisopropyl ether (30 ml) and dried to yield the compound (12) (10.4 g) as a white crystal. Yield from the compound (22):82%

2-Carbamoyloxymethyl-5-(3,5-dichlorophenylthio)-4-isopropyl-1-(pyridin-4-yl)methyl-1H-imidazole (14)

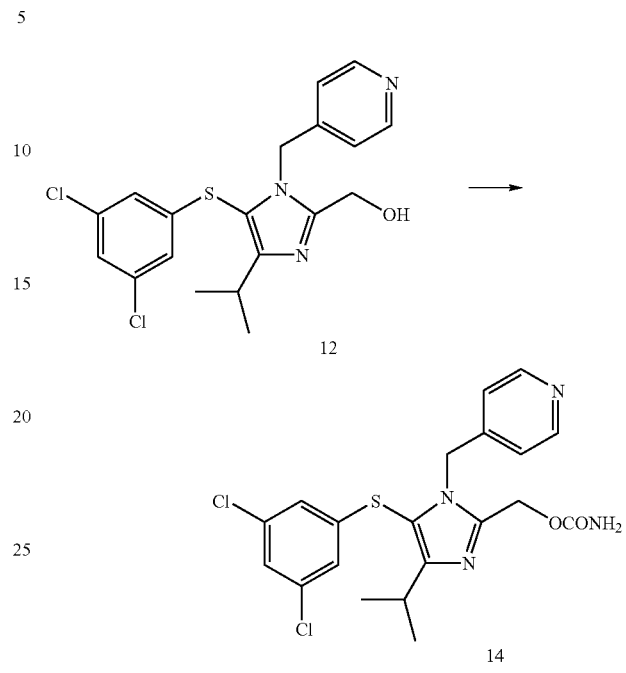

The hydroxy compound (12) (2.00 g, 4.9 mmol) was suspended in ethyl acetate (20 ml). The solution was cooled down to −30° C. under nitrogen atmosphere. To the solution was added dropwise chlorosulfonyl isocyanate (1.66 g, 11.4 mmol) under nitrogen atmosphere at −30° C. for 30 minutes, and the mixture was stirred at the same temperature for 1 hour. To the mixture was added dropwise water (2 ml), and the mixture was warmed up to 0° C. To the mixture were added 35% aqueous hydrochloric acid (2 ml) and methanol (4 ml), and the solution was stirred at 40° C. for 1 hour. The mixture was cooled down to room temperature and neutralized by 20% aqueous sodium carbonate. The organic layer was separated, washed with water concentrated, and dried. To the residue was added methanol (6 ml) for dissolution, then water (6 ml) at room temperature for temperature. The obtained slurry was filtered, washed with 50% aqueous methanol (6 ml) and dried to yield the compound (14) (2.06 g). Yield 93.2%.

$^1$H-NMR (CDCl$_3$-TMS) δ ppm : 1.32 (d, J=6.9 Hz, 6H), 3.17 (sept, 1H), 4.53 (b, 2H), 5.21 (s, 2H), 5.27 (s, 2H), 6.69 (d, J=1.6 Hz, 2H), 6.82 (d, J=5.2 Hz, 2H), 7.06 (t, J=1.6 Hz, 1H), 8.46 (b, 2H). Element analysis (C$_{20}$H$_{20}$Cl$_2$N$_4$O$_2$S.0.5H$_2$O) Calcd. (%):C, 52.16; H, 4.61; N, 12.17; S, 6.96; Cl, 15.42. Found. (%):C, 52.45; H, 4.72; N, 11.73; S, 7.08; Cl, 14.81. 2HCl salt of the compound (14):mp 214–222° C. (dec)

INDUSTRIAL APPLICABILITY

The present invention provides the process for producing arylsulfenyl halide and a precursor thereof, alkyl aryl sulfide, which is useful as a starting material of a pharmaceutical composition, especially an antiviral composition or a composition for treatment of AIDS. The present process is easy to handle, economical, and applicable to a large-scale production.

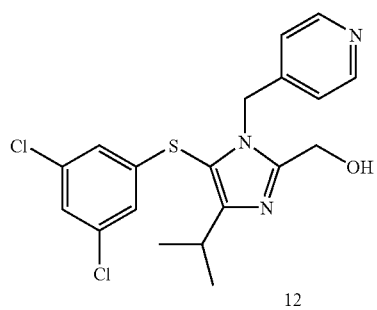

12

The invention claimed is:

1. A process for producing a compound of the formula (IV):

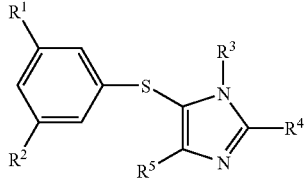

wherein $R^1$ and $R^2$ each independently represents halogen, alkyl, alkoxy, nitro or cyano, $R^3$ represents hydrogen or an organic residue, $R^4$ represents an organic residue and $R^5$ represents hydrogen or an organic residue, which comprises preparing a compound of the formula (II):

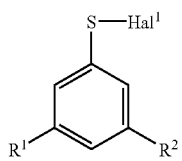

wherein $Hal^1$ represents halogen and $R^1$ and $R^2$ are as defined above, by a process which comprises allowing a halogenating agent to react with a compound of the formula (I):

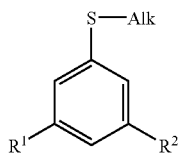

wherein Alk represents isopropyl or tert-butyl and $R^1$ and $R^2$ are as defined above, then reacting the compound of the formula (II) with a compound of the formula (III):

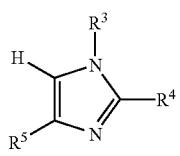

wherein $R^3$, $R^4$ and $R^5$ are as defined above.

2. A process for producing a compound of the formula (IV):

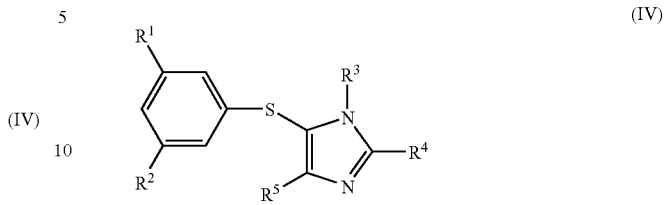

wherein $R^1$ and $R^2$ each independently represents halogen, alkyl, alkoxy, nitro or cyano, $R^3$ represents hydrogen or an organic residue, $R^4$ represents an organic residue and $R^5$ represents hydrogen or an organic residue, which comprises preparing a compound of the formula (II):

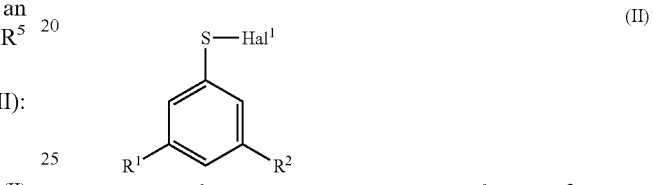

wherein $Hal^1$ represents halogen and $R^1$ and $R^2$ are as defined above, by a process which comprises preparing a compound of the formula (I):

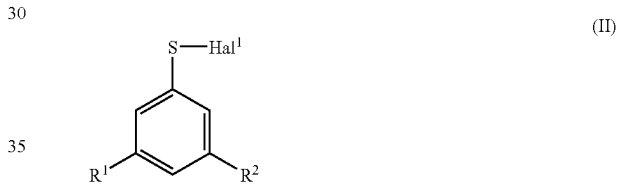

wherein Alk represents isopropyl or tert-butyl and $R^1$ and $R^2$ are as defined above, by a process which comprises reacting a compound of the formula (V):

Alk-SH           (V)

wherein Alk is as defined above, with a compound of the formula (VI):

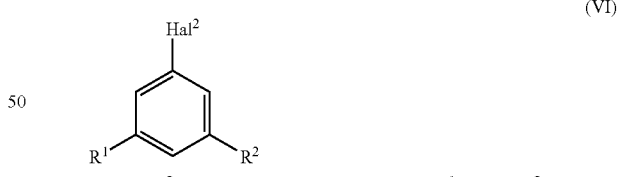

wherein $Hal^2$ represents halogen and $R^1$ and $R^2$ are as defined above, in the presence of phase transfer catalyst and a base, then allowing a halogenating agent to react with the compound of the formula (I), then reacting the compound of the formula (II) with a compound of the formula (III):

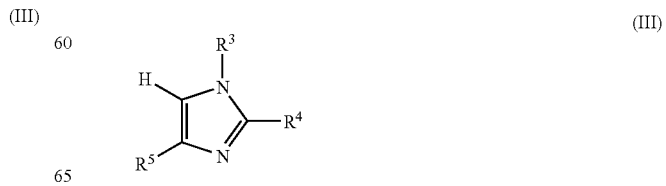

wherein $R^3$, $R^4$ and $R^5$ are as defined above.

3. The process according to any one of claims 1 to 2 wherein $R^1$ and $R^2$ each independently represents halogen.

4. The process according to claim 1 or 2 wherein $R^3$ represents hydrogen or optionally substituted heteroarylalkyl, $R^4$ represents -A-X wherein A represents —Ch$_2$OCH$_2$— or —CH$_2$O)—, X represents optionally substituted aryl or —COB wherein B represents optionally substituted alkyl, optionally substituted alkoxy, optionally substituted aryl or optionally substituted amino and $R^5$ represents optionally substituted alkyl.

* * * * *